(12) United States Patent
Ahn

(10) Patent No.: US 8,337,862 B2
(45) Date of Patent: Dec. 25, 2012

(54) METHOD FOR TREATING KNEE JOINT PAIN CAUSED BY SAPHENOUS NERVE ENTRAPMENT

(75) Inventor: Kang Ahn, Seoul (KR)

(73) Assignee: Ipsen Biopharm Limited, Wrexham (GB)

( * ) Notice: Subject to any disclaimer, the term of this patent is extended or adjusted under 35 U.S.C. 154(b) by 298 days.

(21) Appl. No.: 12/506,622

(22) Filed: Jul. 21, 2009

(65) Prior Publication Data

US 2009/0317426 A1  Dec. 24, 2009

Related U.S. Application Data

(62) Division of application No. 11/630,099, filed as application No. PCT/KR2005/002002 on Jun. 27, 2005, now abandoned.

(30) Foreign Application Priority Data

Jun. 28, 2004 (KR) .................................. 2004-48889

(51) Int. Cl.
*A61K 39/08* (2006.01)
(52) U.S. Cl. .................................................. 424/239.1
(58) Field of Classification Search .................... None
See application file for complete search history.

(56) References Cited

U.S. PATENT DOCUMENTS

| | | | | |
|---|---|---|---|---|
| 2003/0054975 | A1* | 3/2003 | Voet | 514/2 |
| 2003/0143249 | A1* | 7/2003 | Lamb | 424/239.1 |
| 2003/0224019 | A1 | 12/2003 | O'Brien | |
| 2004/0028704 | A1 | 2/2004 | Pappagallo | |
| 2004/0038874 | A1 | 2/2004 | Omoigui | |
| 2006/0178354 | A1* | 8/2006 | Lucas | 514/178 |

FOREIGN PATENT DOCUMENTS

| | | | |
|---|---|---|---|
| WO | 0178760 | A2 | 10/2001 |
| WO | WO 01/78760 | * | 10/2001 |
| WO | 03/094808 | | 11/2003 |

OTHER PUBLICATIONS

Morganti et al (Journal of American Academy of Orthopaedic Surgeons, Mar.-Apr. 2002.*
Boroff, D.A. et al, Journal of Physiology, 1974, vol. 240, pp. 227-253, Observation son theaction of Type A botulinum toxin on Frog neuromuscular junctions.*
Von Wendt, L.O. et al, European Journal of Paediatric Neurology, 1999, vol. 3, pp. 175-176, Botulinum toxin for amelioration of knee contracture in Duchenne muscular dystrophy.*
Bambrick, Linda et al, Journal of Physiology, 1987, vol. 382, pp. 69-88, Acetylcholine receptors and sodium channels in denervated and botulinum toxin treated adult rat muscle.*
Sonographic Imaging for Guiding Botulinum toxin Injections in Limb muscles, vol. 4(5), Nov./Dec. 2004, pp. 1-4.*
Saitou, k et al, Journal of Human Ergology, Dec. 2000, vol. 29(1-2), pp. 35-52, Innervation zones of the upper and lower limb muscles estimated by using multichannel surface EMG.*
J.M.A. Mens, "Pseudo-Arthritis of the Knee Caused by Compression Neuropathy of the Saphenous Nerve," Ned Tijdschr Geneeskd Jul. 11, 1987: 131(28): 1215-8.
Lew C. Schon, M.D. and Donald E. Baxter, M.D., "Neuropathies of the Foot and Ankle in Athletes," Clin. Sports Med. Apr. 1990, 9(2): 489-509.
C.M. Morganti, MD.: Edward G. McFarland, MD; and Andrew J. Cosgarea, MD, "Saphenous Neuritis: A Poorly Understood Cause of Medial Knee Pain." J. Am. Acad. Orthop Surg., Mar.-Apr. 2002, 10(2):130-7.
Burg, D. et al. "Effective Treatment of a Large Muscle Hernia by Local Botulinom Toxin Adminsitration", In Handchir Mikrochir Plast Chir., Mar. 1999, vol. 31, No. 2, p. 75-8.
Evers, S. et al. "Treatment of Headache With Botulinum Toxin A—A Review According to Evidence-Based Medicine Criteria", In Cephalalgia, Nov. 2002, vol. 22, No. 9, pp. 699-710.
Geoffrey Sheean, "Botulinum Toxin for the Treatment of Musculoskeletal Pain and Spasm", In Current Pain Headache Reports, Dec. 2002, vol. 6, No. 6, pp. 460-469.
C. Morganti et al., "Saphenous neuritis: a poorly understood cause of medial knee pain," The Journal of the American Academy of Orthopaedic Surgeons, Mar. 2002, vol. 10, No. 2, pp. 130-137.
S. Mense, "Neurobiological basis for the use of botulinum toxin in pain therapy," Journal of Neurology, Feb. 2004, vol. 251, Suppl. I, pp. 11-17.
K. Ahn et al., "Subcutaneous botulinum toxin type a injection for chronic medial knee pain with osteoarthritis," Anesth. Pain Med., Jul. 2009, vol. 4, No. 3, pp. 221-225.
M. Cui et al., "Subcutaneous administration of botulinum toxin A reduces formalin-induced pain," Journal of Pain, Jan. 2004, vol. 107, No. 1-2, pp. 125-133.
Supplementary European Search Report mailed Jul. 15, 2010 in corresponding European patent application No. EP 05 76 589.
Jabbari et al., "Botulinum toxin A improved burning pain and allodynia in two patients with spinal cord pathology," Pain Medicine, 2003, vol. 4, No. 2, pp. 206-210.
Saishin-Igaku-Daijiten, "Compression neuropathy (entrapment neuropathy, syndrome of entrapment)," Oct. 29, 2001, English translation provided, pp. 1-5.

* cited by examiner

*Primary Examiner* — Albert Navarro
*Assistant Examiner* — Ginny Portner
(74) *Attorney, Agent, or Firm* — Jacobson Holman PLLC

(57) ABSTRACT

A method using a pharmaceutical composition comprising botulinum toxin and a pharmacologically acceptable carrier to treat pain in the knee joint caused by saphenous nerve entrapment. The composition of the present invention is for subcutaneous injection above the medial side of the knee.

4 Claims, No Drawings

METHOD FOR TREATING KNEE JOINT PAIN CAUSED BY SAPHENOUS NERVE ENTRAPMENT

CROSS REFERENCE TO RELATED APPLICATIONS

This application is a divisional of U.S. patent application Ser. No. 11/630,099, filed Jun. 11, 2007, which is a Section 371 National Phase of PCT/KR05/02002, filed Jun. 27, 2005, which are incorporated by reference as if fully set forth.

FIELD OF THE INVENTION

The present invention relates to a pharmaceutical composition comprising botulinum toxin and a pharmacologically acceptable carrier for treating pain in the knee joint by saphenous nerve entrapment. In use, the composition of the present invention is injected subcutaneously above the medial side of the knee.

BACKGROUND

As is well known, a knee joint consists of an inside and an outside. It has often been believed that the knee pain is caused by problems of the inside of the joint. However, receptors, which function to transport pain, are more present around the joint than the inside of the joint. Furthermore, autoradiography reveals that the level of knee injury is not necessarily directly proportional to the level of pain in the knee. With age, a man typically has injury to the inside of the joint while the outside of the joint undergoes various changes.

The saphenous nerve is a nerve that transfers the pain of the medial side of the knee. The entrapment of the nerve also causes pain in the knee. Although the saphenous nerve entrapment can be identified by electroneuromyography, etc., the saphenous nerve is oftentimes not entrapped when the nerve is in a rest state. As such, it is virtually impossible to diagnose the entrapment by electroneuromyography when the nerve is in the rest state. (See, Schon L C, Baxter D E. Neuropathies of the foot and ankle in athletes, Clin Sports Med. 1990 April; 9(2): 489-509, Mens J M. Pseudoarthritis of the knee caused by compression neuropathy of the saphenous nerve, Ned Tijdschr Geneeskd, 1987 Jul. 11; 13 1(28): 1215-8, Morganti C M, McFarland E G, Cosgarea A J. Saphenous neuritis: a poorly understood cause of medial knee pain, J Am Acad Orthop Surg. 2002 March-April; 10(2): 130-7). The saphenous nerve entrapment is a condition that occurs frequently. However, a drug which efficiently treats the pain associated therewith has not been developed.

The anaerobic, gram positive bacterium *Clostridium botulinum* produces a botulinum toxin. Such toxin causes a neuroparalytic illness in humans and animals known as botulism. The effects of botulism typically appear about 18 to 36 hours after eating foods infected with *Clostridium botulinum* spores. The botulinum toxin can apparently pass through the lining of the gut and attack the peripheral motor neurons.

Botulinum toxins have been used in clinical settings for the treatment of neuromuscular disorders characterized by hyperactive skeletal muscles. Botulinum toxin type A has been approved by the U.S. Food and Drug Administration for the treatment of blepharospasm, strabismus and hemifacial spasm. Non-type A botulinum toxin serotypes apparently have lower potency and/or shorter duration of activity than botulinum toxin type A. Clinical effects of peripheral intramuscular botulinum toxin type A are usually seen within one week of injection. A typical duration of symptomatic relief from a single intramuscular injection of botulinum toxin type A averages about three months.

Although techniques for treating pain through the use of botulinum toxin have been developed, the botulinum toxin used in the prior art focused on the effect of the toxin on the acetylcholine per se.

For example, U.S. patent publication 2003/0224019 is directed to the use of botulinum toxin type B for treating pain caused by nerve entrapment. It specifies that the botulinum toxin type B is injected into an area where nerve entrapment occurs. This may also include an area impinging the nerve itself or near the nerve. In the publication, the duration of effect in patients responding to MYOBLOC™ treatment has been observed to be between 12 and 16 weeks at a dosage of 5,000 units or 10,000 units.

The use of botulinum toxin type A has been disclosed in U.S. patent publication 2004/028704. In that publication, the botulinum toxin type A is utilized for treating pain caused from carpal tunnel syndrome. Further in that publication, the botulinum toxin type A is injected into muscles of the hand andor wrist, or the carpal tunnel along the median nerve.

U.S. patent publication 2004/038874 discloses that the botulinum toxin treats pain by blocking acetylcholine andor neurotransmitter rather than directly affecting the receptors. However, it does not specify the area to be injected.

Furthermore, WO 2001/78760 describes a method for treating pain through peripheral administration of botulinum toxin to a patient who is experiencing a nonmuscle disorder related pain. However, the botulinum toxin in that method is not injected into a certain treatment area identified by a physical scientific examination. It is rather randomly injected into a non-specified area, thereby exhausting acetylcholine and controlling pain by a chemically mediated response. Thus, such method is not intended to treat a specific disease.

Although, the prior art references describe that the pain could be treated by using the botulinum toxin, they fail to teach or suggest treating the pain in the knee joint rapidly and effectively through injecting a lower amount of botulinum toxin. Currently, there is a need for a drug which can be applied effectively to treat the pain in the knee joint.

DISCLOSURE OF INVENTION

Technical Problem

The objective of the present invention is to provide a pharmaceutical composition that can treat pain in the knee joint by saphenous nerve entrapment in a more rapid and effective manner, while comprising a smaller amount of active ingredient.

The inventor of the present invention found that the pain in the knee joint caused by saphenous nerve entrapment can be treated more rapidly and effectively by injecting the present composition, which includes the botulinum toxin and a pharmacologically acceptable carrier, into the area having many abnormal hypersensitive receptors. Such area can be identified by palpating the subcutaneous fascia above the medial side of the knee.

Therefore, the present invention provides a pharmaceutical composition comprising botulinum toxin and a pharmacologically acceptable carrier for treating pain in the knee joint caused by saphenous nerve entrapment.

More specifically, the present invention provides a pharmaceutical composition comprising botulinum toxin and a pharmacologically acceptable carrier for treating pain in the knee joint caused by saphenous nerve entrapment, in which such composition is for subcutaneous injection above the medial side of the knee.

Preferably, the composition of the invention is injected into a subcutaneous fascia having densely close hypersensitive receptors and located at the saphenous nervedominating area above the medial side of the knee.

According to the present invention, a smaller amount of botulinum toxin is injected into the knee so that the pain caused by saphenous nerve entrapment thereat can be treated more rapidly and the treating effect can be maintained for at least 4 weeks, preferably 16 weeks, and more preferably 32 weeks.

Preferably, the composition of the present invention comprising botulinum toxin can be injected to multiple points on the subcutaneous fascia located at a hand's breadth above the medial side of the knee. The terms "hand's breadth" above the medial side of the knee signifies a distance of about 15 to 25 cm above the medial side of the knee in which the multiple points of injections are defined, which distance may be varied depending on the patient's height and the like.

The area having many abnormal receptors to which the present composition is injected into can be identified by feeling the skin, tenderness of a patient, skin thickness, etc. in palpating the patient.

Specifically, if there is severe pain when pinching the skin where the saphenous nerve passes underneath, it is believed that saphenous nerve entrapment may cause pain in the knee medial side upon moving. Therefore, pinching the skin area where the saphenous nerve passes underneath can identify certain region that is abnormally hypersensitive to acetylcholine etc. so that botulinum toxin can be injected thereinto. Thus, the possibility of controlling pain by injecting botulinum toxin to the subcutaneous fascia around the knee has been unknown in the art until the development of the present invention.

Technical Solution

The present invention provides a pharmaceutical composition comprising botulinum toxin and a pharmacologically acceptable carrier for treating pain in the knee joint caused by saphenous nerve entrapment.

By botulinum neurotoxin (or botulinum toxin) is meant in the present application a botulinum neurotoxin complex (whether of type A, B, C, D, E, F or G) as well as a high purity botulinum neurotoxin (whether of type A, B, C, D, E, F or G). Botulinum toxin type A includes all types of botulinum toxin type A, including A1, A2 and A3.

By botulinum neurotoxin complex (whether of type A, B, C, D, E, F or G) should be understood in the present application a botulinum neurotoxin (whether of type A, B, C, D, E, F or G) associated with at least another non-toxic protein.

By high purity botulinum neurotoxin (whether of type A, B, C, D, E, F or G) is meant, in the present application, botulinum neurotoxin (whether of type A, B, C, D, E, F or G) outside from complexes including at least another protein. In other words, a high purity botulinum neurotoxin (type A, B, C, D, E, F or G) does not contain significant quantities of any other *Clostridium* spp derived protein than botulinum neurotoxin (type A, B, C, D, E, F or G).

The present invention is directed to a method for controlling pain by removing saphenous nerve entrapment which induces pain around the knee joint, and not for treating pain which occurs inside of the joint.

As described above, it is believed that botulinum toxin, used in the prior art for treating pain, paralyzes a muscle by inhibiting secretion of acetylcholine. Thus, it decreases the motility of alpha and gamma moving fibers, thereby controlling the pain. In contrast, the botulinum toxin, a neurophilic material included in the composition of the present invention, causes an immediate nerve reflex. Specifically, it cause such nerve reflex on a hypersensitive acetylcholine receptor and other pain receptors etc., which are present in fascia and muscle around the nerve inducing the entrapment, upon its injection to such fascia and muscle. This relaxes the fascia and muscle by normalizing the hypersensitive receptors. It further controls the pain and improves the motility by normalizing a receptor (C fiber) that transfers signals for excessive pain.

The secretion of acetylcholine is not crucial for the present invention. It takes ordinarily 3 to 5 days for the botulinum toxin to block the secretion of acetylcholine. The present invention aims at inducing nerve reflex by the neurophilic property of the botulinum toxin. However, the present invention can alleviate or remove the pain in a remarkably short time even with a smaller amount of the toxin.

Other advantage of the present invention is that the composition of the present invention does not disturb the normal secretion of acetylcholine without any paralysis of muscles or other soft tissue. In contrast, if the botulinum toxin is used in the conventional pain treatment method, there are several side effects to be considered (e.g., luxation of temporomandibular joint in injecting the toxin to the muscle of the joint). For example, the hypersensitive receptor responds as if many acetylcholine acts thereon even when a small amount of acetylcholine is present.

The conventional botulinum toxin injection is administered deeply in a muscle in order to block secretion of acetylcholine, thereby paralyzing the muscle. In contrast, the present invention does not significantly consider whether or not acetylcholine secretes. It administers the toxin injection in order to block the response of the hypersensitive receptor on secretion of a small amount of acetylcholine, to which the normal receptor does not respond. Therefore, the present invention achieves its desired objective by using a small amount of botulinum toxin and it is not necessary to inject the toxin formulation deeply into the muscle for paralyzing the muscle as in the prior art. Such mechanism and method have not been suggested in any of the publications or documents.

As described above, U.S. patent publication 2003/0224019 discloses that the botulinum toxin type B can be used for treating pain. Further, U.S. patent publication 2004/028704 describes that the pain derived from carpal tunnel syndrome is treated by using the botulinum toxin type A. However, these publications do not suggest any treatment of knee joint pain caused by saphenous nerve entrapment.

Preferably, the pharmaceutical composition of the present invention comprising the botulinum toxin is injected into the subcutaneous fascia, which has densely close hypersensitive receptors, located at the saphenous nerve-dominating area above the medial side of the knee. However, the injected area of the prior art is a tissue impinging the nerve, an interstitial area around the nerve or a connecting tissue around the nerve.

The area to be injected by the pharmaceutical composition of the present invention is the overall area being controlled by a nerve, regardless of the existence of the nerve itself, where the hypersensitive receptors exist. The composition of the present invention is preferably simultaneously injected into multiple points on the subcutaneous fascia regardless of the entrapment point. U.S. patent publication 2003/0224019, on the other hand, injects the botulinum toxin only where nerve entrapment occurs.

The injected area of the muscles of the hand and/or wrist, or the carpal tunnel along the median nerve described in U.S. patent publication 2004/028704, also differ from that of the present invention. This is because the publication does not disclose or suggest the crucial feature of the present invention, namely, the injected area which is the overall area being controlled by a nerve where the hypersensitive receptors exist. This is regardless of the existence of the nerve itself.

Although U.S. patent publication 2004/038874 does not specify an injected area, it is nonetheless different from the present invention. More specifically, it treats the pain by blocking acetylcholine, a neurotransmitter, rather than directly affecting the receptors as in the present invention.

Furthermore, WO 2001/78760 suggests that the pain might be alleviated or treated by administering botulinum toxin to the joint or subcutaneously around the joint. However, the publication does not disclose the use of the botulinum toxin to treat the knee pain caused by saphenous nerve entrapment. Furthermore, the botulinum toxin in this method is injected randomly into non-specified area, and not a certain treatment area identified by a physical scientific examination. Hence, it exhausts acetylcholine and controls pain by a chemically mediated response. Also, it does not suggest the significance of hypersensitive receptor control, and further fails to disclose that the toxin has to be injected into the area where the hypersensitive receptors are densely located.

More particularly, the publication does not disclose or suggest the technical feature of the present invention whereby the physical scientific examination or instrument is used to find an area. It further does not disclose where the hypersensitive receptors are densely located and dominated by saphenous nerve above the knee medial side. That publication also does not disclose that a small amount of botulinum toxin is injected multiply into the subcutaneous fascia of the area to induce nerve reflex and thereafter the disappearance of the receptor hypersensitivity is confirmed by pinching the skin.

The pharmaceutical composition of the present invention, which comprises a significantly smaller amount of botulinum toxin than the dosage used in the prior art, shows a superior effect for alleviating or treating the pain in the knee.

In one particular embodiment of the invention, the botulinum toxin type A that is injected into a subject in need thereof, which is an ingredient of the pharmaceutical composition of the present invention, is shown to have an excellent effect. For example, such superior effect is achieved even in 60 $LD_{50}$ units of dosage, which is a greatly smaller amount than that in the prior art. In the instant application, unless specified otherwise, one $LD_{50}$ unit of botulinum toxin means the median lethal in-traperitoneal dose in a group of 18 to 20 female Swiss-Webster mice weighing about 20 grams each.

More specifically, U.S. patent publication 2003/0224019 utilizing the botulinum toxin type B for treating the pain caused by nerve entrapment describes that the duration of effect in patients responding to MYOBLOC™ treatment has been observed to be between 12 and 16 weeks at dosage of 5,000 units or 10,000 units. It should be noted herein that 20 to 200 $LD_{50}$ units of botulinum toxin type A utilized in one embodiment of the present invention correspond to approximately 300 to 3,000 units of botulinum toxin type B (1,000 units of botulinum toxin type B correspond to approximately 60 $LD_{50}$ units of botulinum toxin type A utilized in the present invention).

Therefore, U.S. patent publication 2003/0224019 would involve the injection of 300 or 600 $LD_{50}$ units of botulinum toxin type A. This clearly means that the present invention injects a significantly smaller amount of botulinum toxin type A than that of the publication.

In addition, the present invention relieves the pain in the knee much more quickly than the prior art. Unlike the prior art wherein the pain is relieved 2 to 3 days after injection, the composition of the present invention can remove the pain immediately after the injection of the composition. This means that the hypersensitivity of the receptor is changed.

Most of the injected subjects were confirmed to have disappeared hypersensitivity. In case that the cause for producing the hypersensitivity is more complicated in some patients (e.g., secondary hyperalgesia), such change of the receptor hypersensitivity is meaningless. That is, if such patients again show pain several days after injection, then there is a secondary reason for inducing receptor hypersensitivity. This means that the composition of the present invention has no effect on the pain. This is for the following reason. A small amount of botulinum toxin temporarily changes the hypersensitivity of the receptor, which makes the receptor normalized. If the normalized receptor is affected by a secondary reason, then the normalized receptor becomes hypersensitive again.

Unless such situation occurs, however, the hypersensitivity of the receptor may be maintained for a substantial period or permanently. Since the mechanism of the pain treatment is to change the hypersensitivity of the receptor, the receptor having the changed hypersensitivity is not affected by the retention effect or action period of the drug.

The hypersensitive acetylcholine receptor responds to acetylcholine of $\frac{1}{1000}$ or less of the normal amount of acetylcholine, thereby inducing contracture of the muscle. The composition of the present invention intends to render the abnormal receptor that responds to such small amount of acetylcholine changed directly. That is, the composition of the present invention functions not to block secretion of acetylcholine or other chemicals. Rather, it normalizes the hypersensitive receptor that responds to the chemicals sensitively regardless of their secretion, and that transfers to the nerve the incorrect information as if large amounts of chemicals are secreted even when small amounts were secreted. Thus, it is not necessary to use the botulinum toxin in large dosage, which paralyzes the muscle.

As explained above, the pharmaceutical composition of the present invention comprising the botulinum toxin has a superior effect for alleviating or treating the knee pain by removing the hypersensitivity of the abnormal receptor.

The knee joint pain by saphenous nerve entrapment results from the nerve entrapment caused by entrapping the saphenous nerve in the state where muscle or fascia around saphenous nerve is contractured. The pain of knee medial side is felt when walking and disappears during rest. The present invention elucidated that the botulinum toxin normalizes the several hypersensitive receptors, including the acetylcholine receptor, by directly affecting such receptors. This induces nerve reflex and a smaller amount of the toxin can be used to treat the knee joint pain in a remarkably short time by reducing the contracture of muscle and fascia entrapping or stimulating saphenous nerve branch.

The inventor of the present invention investigated the pain alleviating effect of botulinum toxin by injecting the toxin to patients who suffer from the knee joint pain. As a result, it could be confirmed that the knee joint pain of the patients was significantly decreased in a short period after injecting the toxin.

When the pharmaceutical composition of the present invention is used in actuality unit dosage forms which are suitable for injection are formulated and administered according to the conventions of the pharmaceutical field.

The suitable injection formulation, in addition to botulinum toxin as the pharmacologically active agent, may contain one or more pharmacologically non-active conventional carrier mediums (e.g., excipients such as starch, lactose, carboxymethylcellulose, kaolin, and the like; stabilizers such as albumin, gelatin, and the like; binders such as alcohol, glucose, arabic gum, tragacanth gum and the like; disintegrants such as starch, dextrine, sodium alginate, and the like; and lubricants such as talc, stearic acid, magnesium stearate, liquid paraffin, and the like).

For example, the injection formulation of the present invention can be prepared by mixing botulinum toxin obtained by purifying cultures of Clostridium botulinum. This is through using a known method with albumin solution as a stabilizer and lactose as an excipient in a physiological saline solution.

The dosage of the composition according to the present invention depends on various factors such as patient's degree of knee pain, time of onset of knee pain, age, etc. However, for an average adult, a total of about 20 to 200, preferably about 30 to 100, and more preferably about 40 to 70 $LD_{50}$ units (e.g., about 60 to 70 $LD_{50}$ units) of the botulinum toxin type A are injected into multiple points on the subcutaneous fascia around saphenous nerve having the hypersensitive receptors. A single treatment produces the sufficient effect for removing the pain. However, if the skin pinched by the fingers is thick and the pain is serious, the botulinum toxin can be injected in larger amounts beyond the above specified units.

As for the dosage of various types of botulinum toxins (e.g., B, C, D, E, F and G) that can be used in the present invention, a person skilled in the art could easily determine the appropriate dosage of each type of the botulinum toxin based on that of the botulinum toxin type A. For example, when figuring out the suitable dosage of the botulinum toxin B according to the dosage of the botulinum toxin type A of the present invention, it should be noted herein that about 300 to 3,000 units of botulinum toxin type B correspond to about 20 to 200 $LD_{50}$ units of botulinum toxin type A. This is based on the fact that 1,000 units of botulinum toxin type B correspond to approximately 60 $LD_{50}$ units of botulinum toxin type A of the present invention.

The pain of the patient may be deemed to have been treated sufficiently by normalization of the hypersensitive receptor (1) if the pain disappears when the skin is pinched immediately after injection of the composition and (2) if the thickly seized region of the skin disappears.

The present invention is further described with the following example. This example is intended only to illustrate the present invention and should not be construed as limiting the present invention in any way.

Advantageous Effects

The composition comprising the botulinum toxin according to the present invention has a superior effect of more rapidly alleviating or treating the knee joint pain even in a smaller dosage so that the composition can be utilized in treating pain in the knee joint.

BEST MODE FOR CARRYING OUT THE INVENTION

The effect of the pharmaceutical composition of the present invention for treating the knee joint pain caused by the saphenous nerve entrapment was investigated through the following test.

EXAMPLE 1

Double-blinded placebo-controlled clinical trial was carried out for 89 patients of chronic knee pain. This was to compare the effect of botulinum toxin type A injection with that of a physiological saline solution in Chronic Pain Center of Cha hospital located in Seoul, South Korea.

The botulinum toxin type A injection used in the test was prepared by dissolving DYSPORT™, which is commercially available from Ipsen Limited (England), comprising 500 units of botulinum toxin type A with 20% albumin solution (0.625 µl) and lactose (2.5 mg) in the physiological saline solution of 18 cc.

The injected areas were identified by Pinch-roll test where the skin fascia governed by the saphenous nerve is pinched and rolled by the finger. The specified areas having the hypersensitive receptors were found to be approximately 5 to 12 areas per patient knee. The specified areas were further pinched to confirm more sensitive points and the above prepared formulation was injected to the points in dosage of 5 or 10 units of the toxin type A per injection point. The total dosage per treatment was about 60 units based on DYSPORT.

The group, to which botulinum toxin type A was injected, did not show a significant difference from the control group with respect to pain level, arthritis severity on X-ray photograph, etc. before the injection. Based on 10 cm-Visual analogue scale (VAS) with 10 representing the pain score before the treatment, the control group showed a slight decrease from about 8.1 to about 6.03 three weeks after injection of the saline solution. Meanwhile, the pain was remarkably improved from 7.35 to 4.59 in the botulinum toxin type A injected group. As such, it was observed that knee extension, which is a major parameter in joint pain and arthritis of the aged, was significantly improved.

TABLE 1

Difference of VAS after end of treatment

| | Control | botulinum toxic type A group | p value |
|---|---|---|---|
| Baseline | 8.10 ± 2.16 | 7.35 ± 2.44 | NS |
| After 1 week | 6.75 ± 2.64 | 5.83 ± 2.45 | NS |
| After 3 weeks | 6.03 ± 2.35 | 4.59 ± 2.69 | <0.05 |

TABLE 2

Difference of flexion contracture after end of treatment

| | Control | botulinum toxic type A group | p value |
|---|---|---|---|
| Baseline | 17.1 ± 6.50 | 13.4 ± 6.54 | NS |
| After 1 week | 16.9 ± 6.30 | 12.1 ± 5.71 | <0.05 |
| After 3 weeks | 17.2 ± 5.36 | 12.1 ± 6.30 | <0.05 |

As seen from Table 2, the control group showed no knee extension three weeks after being injected with the saline solution. Statistically, however, the botulinum toxin type A group was found to show significant knee extension.

INDUSTRIAL APPLICABILITY

As evidenced by the above tests, the composition comprising the botulinum toxin according to the present invention has a superior effect of more rapidly alleviating or treating the knee joint pain even in a smaller dosage so that the composition can be utilized in treating pain in the knee joint.

What is claimed is:
1. A method for treating knee joint pain caused by saphenous nerve entrapment in a subject, the method comprising:

identifying at least one area having abnormal hypersensitive receptors by pinching the skin of the subject with saphenous nerve entrapment where the saphenous nerve passes underneath, providing a pharmaceutical composition comprising about 40 to 70 LD50 units of a botulinum toxin and a pharmacologically acceptable carrier; and injecting 5 or 10 LD50 units of the pharmaceutical composition subcutaneously into multiple points in said at least one area having abnormal hypersensitive receptors, thereby removing the pain immediately by normalization of the hypersensitive receptors.

2. The method of claim 1, wherein the botulinum toxin is a botulinum toxin Type A.

3. The method of claim 1, wherein said multiple points are 5 to 12 points.

4. The method of claim 1, wherein the pharmaceutical composition comprises about 60 $LD_{50}$ units of the botulinum toxin.

* * * * *